(12) United States Patent
Simpson et al.

(10) Patent No.: US 8,836,925 B2
(45) Date of Patent: Sep. 16, 2014

(54) IMAGING CRYSTALLINE DOMAINS OF SMALL MOLECULES

(75) Inventors: Garth J. Simpson, West Lafayette, IN (US); Duangporn Wanapun, New London, CT (US); Lynne S. Taylor, West Lafayette, IN (US); Umesh S. Kestur, North Brunswick, NJ (US); Scott J. Toth, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/464,379

(22) Filed: May 4, 2012

(65) Prior Publication Data

US 2013/0057848 A1 Mar. 7, 2013

Related U.S. Application Data

(60) Provisional application No. 61/483,473, filed on May 6, 2011.

(51) Int. Cl.
*G01N 21/00* (2006.01)
*G01N 21/63* (2006.01)

(52) U.S. Cl.
CPC .................................. *G01N 21/636* (2013.01)
USPC ............................................................ 356/30

(58) Field of Classification Search
USPC ............. 356/30, 73, 300, 301, 318, 417, 419; 378/31, 53; 424/489
See application file for complete search history.

(56) References Cited

U.S. PATENT DOCUMENTS

| | | | |
|---|---|---|---|
| 5,515,169 A * | 5/1996 | Cargill et al. ................. | 356/417 |
| 2003/0151742 A1 * | 8/2003 | Silvermintz et al. .......... | 356/318 |
| 2005/0213089 A1 * | 9/2005 | Margalith et al. ............. | 356/300 |
| 2006/0238745 A1 * | 10/2006 | Hashimoto et al. ............. | 356/73 |
| 2007/0218139 A1 * | 9/2007 | Smith et al. .................... | 424/489 |
| 2008/0100834 A1 * | 5/2008 | Kung et al. .................... | 356/301 |
| 2009/0232276 A1 * | 9/2009 | Kogan et al. .................... | 378/53 |
| 2010/0195695 A1 * | 8/2010 | Van De Kerkhof et al. .... | 374/31 |
| 2010/0201988 A1 * | 8/2010 | Kiesel et al. ................... | 356/419 |

* cited by examiner

*Primary Examiner* — Tarifur Chowdhury
*Assistant Examiner* — Jamil Ahmed
(74) *Attorney, Agent, or Firm* — Brinks Gilson and Lione

(57) ABSTRACT

An apparatus and method for performing volume scanning of a sample comprised of chiral materials disposed in a matrix of non-chiral materials is disclosed. A laser is raster scanned in a plane of the volume such that the intensity of energy in the focal region is sufficient to generate second harmonic (SHG) energy. This energy is detected and may be processed into three dimensional images of the volume. The raster pattern is repeatedly stepped over an area of the sample so as to produce three dimensional images of time-dependent processes.

22 Claims, 10 Drawing Sheets

IMAGING CRYSTALLINE DOMAINS OF SMALL MOLECULES

The present application claims the benefit of priority to U.S. provisional application Ser. No. 61/483,473 filed on May 6, 2011 which is incorporated herein by reference in its entirety.

STATEMENT REGARDING FEDERALLY SPONSORED RESEARCH OR DEVELOPMENT

This invention was made with U.S. government support under a grant or contract nos. MRI-0922987 and CHE-0722558 awarded by the National Science Foundation. The government has certain rights in the invention.

TECHNICAL FIELD

This application may relate to the use of an apparatus for generating second harmonic light energy in a sample to measure properties of chiral materials.

BACKGROUND

Crystallization in amorphous solids can be influenced by preparation methods, formulation ingredients, and storage conditions e.g. temperature and humidity. The solid-state form of an organic powder may influence both its chemical and physical properties. For example, the bioavailability of an active pharmaceutical ingredient may change substantially depending on the solid-state form, with even a trace residual crystallinity significantly affecting shelf life.

Understanding of solid-state phase heterogeneity is currently limited in large part by an inability to accurately quantify the trace crystallinity (<1%) of small organic molecules. Studies of solid state phase transformations, especially in solid powders, have been performed using powder X-ray diffraction (PXRD), Raman spectroscopy, infrared spectroscopy, and differential scanning calorimetry (DSC). Although the detection of low levels of crystallinity (~0.2%) has been demonstrated with X-ray diffraction, this level of sensitivity requires high-energy X-rays generated by a synchrotron source and is not suitable for routine analysis. Furthermore, the aforementioned methods provide only ensemble-averaged properties, with no microscopic information (e.g., crystal size distributions, crystal nucleation kinetics, or the like), which can be important in mechanistic studies.

An ability to detect the crystal fraction in an amorphous phase, when the crystal fraction is present at low amounts may allow for the detection of residual crystalline solid that is present as a result of incomplete vitrification. Residual crystal seeds may induce and accelerate crystallization via heterogeneous nucleation, which can give rise to biased results especially when crystallization kinetics and mechanism are of interest. Also, detection of crystallinity at sub-percent level can facilitate the screening and designing of the optimal conditions for crystallization control.

One method of introducing phase heterogeneity within organic powders is by mechanical grinding, which has been widely used as a means for reduction of particle size and synthesis of new materials. For pharmaceutical applications, milling has been employed to enhance the dissolution rate through particle size reduction achieved by mechanical milling and this is sometimes performed at cryogenic temperatures (cryomilling) to minimize local heating. Previous studies have shown that mechanical grinding can result in a loss in crystallinity, a phenomenon observed both in inorganic materials and organic compounds that may result in a mixture of solid-state phases within the sample. The loss of crystalline order in active pharmaceutical ingredients (APIs) during mechanical milling may be deleterious since the loss of crystalline order affect the physical and chemical stability of the drug, which may affect the shelf-life of pharmaceutical products. Typically, mechanical grinding induces solid-state phase transformations as a result of the high shear forces experienced by the material, which may lead to a higher energy defective crystalline material which may subsequently undergo a crystal-to-glass transformation.

Although the effects of mechanical processing have been widely documented, aspects of the process remain unknown for organic systems. Studies of mechanically-induced crystallinity loss are generally performed using X-ray diffraction or thermal analysis techniques. The reduction in the intensity of the Bragg peaks in combination with the presence of a diffuse halo is a common characteristic of increasing disorder within a material. A diffuse halo can, however, arise from different macro/nanoscopic orientation described as thermodynamic disordering: e.g., as observed for melt quenches of organic crystal; or, kinetic disordering whereby the long range crystalline order is reduced to the short-range nanocrystalline domains.

Another method of introducing phase heterogeneity is through the formation of crystals within homogeneous amorphous matrices, including glasses and polymers in the form of powders or tablets. The use of amorphous materials is widespread in the design of pharmaceutical formulations, most typically used to kinetically prevent crystal formation by slowing molecular diffusion. Characterizing nucleation and crystallization kinetics in such matrices is important in making to shelf-life assessments in accelerated stability investigations.

SUMMARY

An apparatus for measuring second harmonic generated (SHG) signals, is disclosed. The apparatus includes a coherent optical source producing a light beam having a first wavelength. The light beam is processed by a raster scan generator which may, for example, have a plurality of mirrors disposed and controlled to produce a raster pattern. The light beam may directed onto the sample using a mirror, which may be a dichroic mirror if both forward and backward propagating SHG energy is to be detected. A sample holder is provided to hold the material sample, and may be used to position the sample with respect to an objective lens that focuses the light beam at a point in the sample.

The focal point may be moved in depth by either translating the sample holder in a direction longitudinal to the light beam, or the focal point may be controlled by similarly moving the objective lens. The forward propagated SHG energy is passed through a filter, which may be an edge filter or bandpass filter that passes light of half of the wavelength of the incident light beam so as to impinge on a photodetector. Where backscattered SHG intensity is to be detected, the mirror may be a dichroic mirror. A conventional mirror may be used if backward scattered SHG intensity is not being measured.

The raster scan field-of-view is positioned at various places on the sample and repeated images are obtained of the sample volume so as to visualize time-dependent physical processes. The temperature of the sample may be controlled during the measurement period.

In another aspect, a method of measuring crystalline structures disposed in an amorphous matrix is disclosed, the method including the steps of: providing a second harmonic generation (SHG) apparatus, the apparatus comprising: a coherent light source; a positionable sample holder; a raster scan device to direct light of the coherent light source onto the sample holder; an optical detector, configured to detect energy at half of the wavelength of the coherent light source; and disposing a sample in the sample holder. The SHG apparatus is operated such that light from the coherent light source is focused at a plurality of selectable depths in the sample and raster-scan SHG signal amplitude data at depths of the selectable depths is obtained. The area of the sample being measured is greater than that of the field-of-view of the raster scan device, and the sample holder and a focusing objective are repeatedly repositioned with respect to each other during the measurements so as to measure a time-dependent process.

DESCRIPTION

Figure 1:
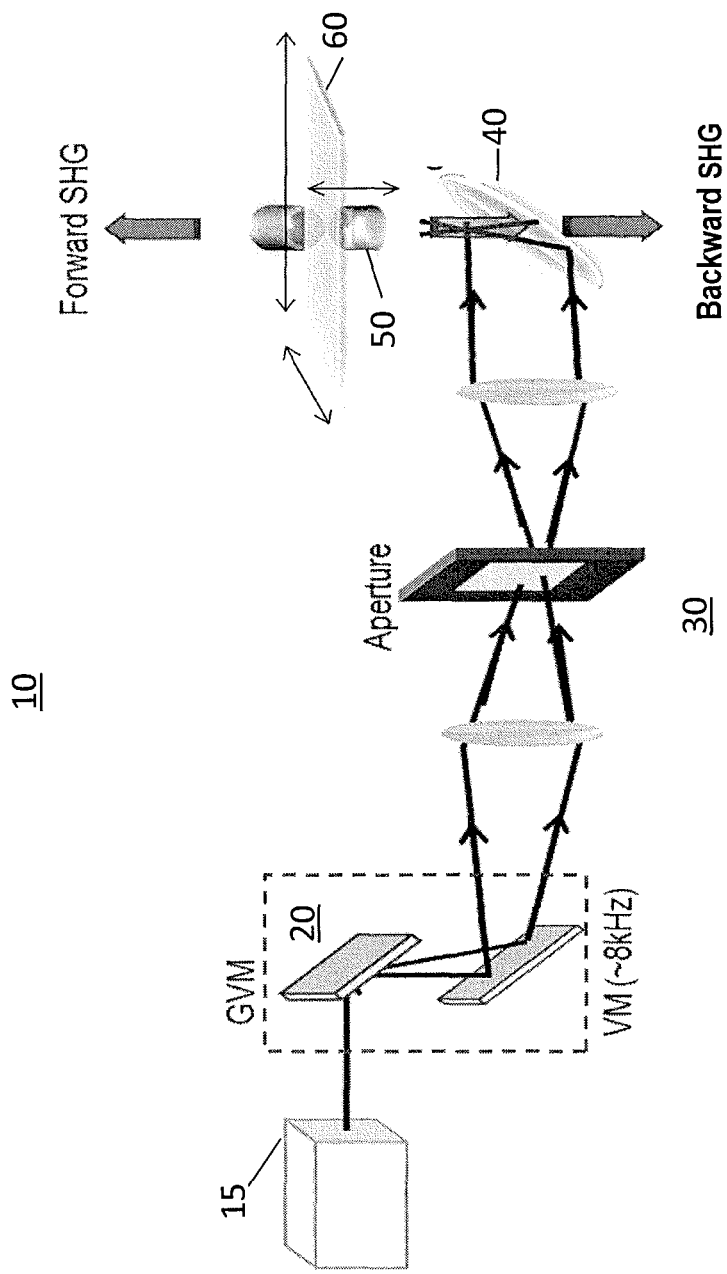
FIG. 1 is a simplified block diagram of the SONICC instrument incorporating combined beam-scanning and sample-scanning for API analysis.

Exemplary embodiments of the apparatus and method may be better understood with reference to the drawings, but these embodiments are not intended to be of a limiting nature. In the following description, numerous specific details are set forth in order to provide a thorough understanding of the present invention which, however, may be practiced without some or all of these specific details. In other instances, well known process operations have not been described in detail in order not to unnecessarily obscure the description.

Second-order nonlinear optical imaging of chiral crystals (SONICC) may be used to characterize the relative crystallinity within powders of a pharmaceutically-relevant organic compound. In the presence of intense optical field: e.g., an ultrafast laser, nonlinear optical interaction between light and matter can occur, resulting in second order harmonic generation (SHG). The nonlinear light-matter interaction that occurs at high intensities converts the light energy at fundamental energy (wavelength) into light at twice the energy (half the fundamental wavelength). In the examples herein, a fundamental excitation wavelength centered at 800 nm was used, and SHG signals at 400 nm were detected.

As a coherent process, SHG may arise by symmetry in certain classes of assembled systems lacking inversion symmetry. Therefore, SHG is "bulk allowed" for the majority of chiral crystals (e.g., crystals comprised of a unit cell with a non-superimposible mirror image), including a significant number of active pharmaceutical ingredients (APIs) crystals. A known exception to this phenomenon is the cubic gyroidal symmetry class (crystal point group of O). On the other hand, in the presence of inversion symmetry, local SHG generated from individual molecules may be canceled by SHG having an out-of-phase relationship generated by neighboring units, resulting in negligible observed SHG. For example, racemic co-crystals containing two enantiomeric isomers in a unit cell demonstrate no observable SHG. In addition to racemic crystals, isotropic systems (e.g., a liquid, a solution, or an amorphous glass) generate no observable coherent SHG, due to destructive interference of the molecular SHG response, resulting in no observable coherent SHG. Based on these principles, SONICC can be applied to sensitively and selectively detect chiral crystals within complex and highly scattering amorphous solids.

Herein, SONICC is applied for the characterization of bulk powdered preparations, for rapid quantitative assessment of trace crystallinity (<1%).

Using SONICC to quantify trace crystallinity within bulk scattering powders may enable characterizing crystallization behavior in powders. The SONICC apparatus described herein permits rapid visualization and measurement of time dependent solid-state phase transformations with both macroscopic and microscopic information, which can provide insight into the mechanisms bridging the microscopic driving force regime governing crystal nucleation and the growth and macroscopic average observables in solid state crystallization.

The effects of mechanical grinding on crystallinity reduction for a low-molecular-weight organic molecule were investigated using X-ray diffraction and SONICC. The results presented herein show that the crystallinity loss exhibits a first order dependence with respect to milling time. In the microcrystal regime (volume smaller than 3200 $\mu m^3$), crystal size distributions estimated using SONICC show no statistically significant change in the crystal size distribution as a function of milling time, suggesting that milling is a method whereby an intact microcrystal may directly be rendered amorphous.

The SONICC method permits measurement of the exponential time decrease in crystallinity over a range of 3 decades of percentage crystallinity, down to a residual crystallinity level of 0.04%. The disordered state obtained by exhaustive cryomilling also appears to contain ordered domains that are larger than critical nucleation size, but below the detection limit of SONICC. The presence of such domains may provide a barrier-less nucleation source resulting in rapid crystallization, the kinetics of which depends only on crystal growth.

Compared to alternative methods commonly used for API powder characterizations, the SONICC technique described herein may have practical advantages. When crystal formation arises in highly localized regions, bulk powder analyses (e.g., PXRD, solid-state NMR, Raman spectroscopy, or the like) integrate the measured values over relatively large probe volumes. In contrast, microscopy methods such as SONICC provide probe volumes commensurate with those arising during early stage crystallization. SONICC also has an advantage of rapid acquisition times, with frame rates of a few seconds used in these studies and video-rate data acquisitions being possible, enabling studies of relatively fast crystallization kinetics. The large area covered by repositioning the field-of-view of the detector and raster scanning enables an increase in the amount of data taken, particularly when events are sparsely distributed over a volume. In contrast, Raman microspectroscopy can require several minutes or hours for acquisition of a single high-resolution image, and solid-state NMR can be similarly time-consuming.

SHG images were acquired using a system configured to perform beam raster scanning with a resonant vibrating mirror (Electro-Optical Products, ~8 kHz) to direct the beam along a fast-axis scan, and a Cambridge galvanometer for slow-axis scanning. Single-image frame scanning with 1000 averages per line was completed in 25 seconds. The depth-of-field and spot size were measured to be ~20 µm and ~2 µm, respectively.).

A schematic diagram of the instrument 10 is shown in FIG. 1. A laser 15 provides a source of coherent light which is directed onto an optical raster scanning device 20 and then directed by an optical system 30 having a plurality of lenses onto a dichroic mirror 40 such that an objective lens 50 brings the light beam to a focal point in the sample being positioned by the sample holder 60. SHG light that is forward scattered is detected by a detector after filtering to reject light at the source wavelength and pass light at half of the source wavelength. Backscattered (epi-scattered) SHG light passes through the dichroic mirror without reflection, and may be detected by another detector. A filter may be positioned between the dichroic mirror and the second detector if needed. The detected photons are amplified and processed to yield a raster image of the sample volume, using data and signal processing as is known in the art. The dichroic mirror 40 may be replaced by a conventional mirror, or omitted, if only forward propagating SHG light is to be detected.

Because SHG intensity scales with the square of the incident light intensity, only the laser light that reaches the focal plane significantly contributes to the detected signal. SHG intensity is proportional to the $4^{th}$ power of the beam waist and any SHG light that is detected can thus be assumed to have arisen from within the focal volume, such that image resolution is not substantially degraded even in highly scattering media. Both forward propagating and backwards propagating (epi) SHG light may be measured as a function of depth (Z-axis) in a sample comprising scattering elements and the crystalline structures to be measured. The lack of SHG response from the matrix in which the crystals are found contributes to a high signal-to-noise ratio of the resultant image.

The Z-axis scanning was performed using an OptiScan motorized focus control (Prior Scientific, Rockland, Mass.) with 20 µm step size. The images were acquired with a resolution of 4×4×20 µm$^3$. The incident optical beam was generated by a Spectra-Physics (Newport Corp., Invine, Calif.) Mai Tai laser, 100 fs, 80 MHz, with 20 mW average power at 800 nm, focused onto the sample using a 10× objective (N.A.=0.3). Alternatively, the Z-axis scanning may be performed by translating the sample stage in the Z direction.

The instrumental design includes the combination of beam-scanning for measurements within a sample position with sample/objective scanning to increase the total volume of the sample probed, and scanning the sample in layers using the properties of the SHG response described above so as to identify the Z-axis position of the measured response. This permits forming a three dimensional image of the sample.

For a given fixed XYZ position of the sample, the focused beam was rapidly swept through the field-of-view at a particular Z value using a combination of the resonant mirror and galvanometer. A sequence of images was then acquired as the focal plane was translated through the sample along the Z-axis. Finally, sample scanning was performed within the X-Y plane with coarse repositioning at several locations. Acquisition of a complete time-dependent data set was achieved by repeating this cycle (beam scanning at each particular value of Z, repeating the beam-scanning measurements at a predefined set of Z-positions to acquire a sequence of Z-plane images, and then repeating the entire procedure for multiple XY locations within the sample regime).

In addition, temperature control by a Linkam Scientific Instruments Ltd. (Guildford, UK) TMS-94 controller with THMS 600 heating stage was combined with the beam and sample scanning in order to assess the influence of temperature on the nucleation and crystallization behavior of APIs in powders, amorphous matrices, and tablets. This apparatus enables monitoring crystal nucleation and growth within a bulk scattering powder; while improving the statistics of nucleation detection by rapid sampling of the selected volume being observed.

The use of relatively low magnification in this specific configuration allowed measurements over a large field-of-view, while the low laser power of 20 mW was selected to provide a linear dynamic range for all percentage values of crystallinity expected during image acquisition. However, other combinations of parameters may be found useful.

The SHG was collected with dichroic mirrors, with narrow band-pass filters (Chroma Technology, Bellows Falls, Vt.; HQ400/20 m-2p) centered at about 400 nm, to reject the incident beam wavelength. The SHG signals were detected by photomultiplier tubes (Burke, XP 2920PC) with photon counting electronics (Becker-Hickl, Berlin Germany; PMS 400A) with the relative collection efficiencies the detectors calibrated using the two-photon excited fluorescence from Chroma standard slides. SHG images were analyzed using ImageJ (available at http://rsb.info.nih.gov/ij; developed by Wayne Rasband, National Institutes of Health, Bethesda, Md.).

Backward (epi)-propagated SHG light intensity was used to estimate the crystal fraction within the sample powders. The average SHG intensity over the field-of-view for each sample was normalized with respect to the average SHG intensity of 100% crystalline griseofulvin to estimate the relative crystallinity. Since the SHG intensity response of a particular crystal depends on both size and orientation of the crystalline domains, a direct estimate of macroscopic crystallinity from SHG intensity will be appropriate for measurements probing a stochastic distribution of crystal orientations within the probed samples, which may be a reasonable assumption for characterizing the microcrystals within the powder.

SONICC has previously been shown to be sensitive to polymorph transitioning during crystallogenesis. However, no significant evidence for polymorph transitioning was observed in the present studies of griseofulvin, allowing modeling using a two-phase transition between amorphous and crystalline phases.

X-ray diffraction data were obtained using Cu—Kα radiation using a Shimadzu XRD-6000 powder diffractometer (Shimadzu Scientific Instruments, Columbia, Md.) operating at 40 kV and 30 mV. For each sample, the X-ray measurements were conducted in a scan range of 5-35° angles (2θ) at a scan rate of 4° C./min with a step size of 0.04° in an aluminum sample holder. The [1 1 1] peak of a Si-standard sample between 28.423-28.463° was used as an external standard. Degrees of crystallinity of the griseofulvin in samples were estimated using the following equation:

$$\text{Degree of crystallinity } (X_c) = \frac{100\, A_c}{A_c + A_a}$$

Here, $A_c$ and $A_a$ represent the respective area contributions from the crystalline and amorphous phases of the sample to the diffractograms. The equation assumes that the experimentally measured crystalline and amorphous X-ray intensities are proportional to the crystalline and amorphous fractions of the samples.

Previous studies have confirmed a linear relationship between integrated peak area and crystal fraction in powdered APIs in general and this method was also applied to estimate the crystallinity of the griseofulvin.

Griseofulvin ((2S,6'R)-7-chloro-2',4,6-trimethoxy-6'-methyl-3H,4'H-spiro[1-benzofuran-2,1'-cyclohex[2]ene]-3,4'-dione) samples were comminuted using a cryogenic mill (6750 freezer mill, Spex Sampleprep, Metuchen, N.J.). Samples weighing approximately 700 mg were sealed into a milling tube and milled for different time periods at a frequency of 10 Hz. The samples were equilibrated at liquid nitrogen temperatures for 5 min prior to milling. Each cycle consisted of milling for 5 or 10 min followed by a cooling interval of 1 min between cycles. The tube was submerged in liquid nitrogen throughout milling to dissipate the heat generated during milling and the levels were maintained by frequent refilling. The milled samples thus obtained were allowed to equilibrate at ambient temperature before they were transferred to a dry nitrogen glove box to minimize the effect of moisture during handling. The samples were sieved to isolate particles in the size range of 50-150 µm to minimize particle size effects on X-ray and SONICC signal intensities.

Amorphous griseofulvin was prepared by maintaining the samples at the melting temperature for 5 min followed by rapidly quenching the samples in liquid nitrogen. The samples were ground lightly in a dry nitrogen glove box and sieved to isolate particles in the size range of 50-150 µm. It may be expected that each particle may generally consist of a conglomerate of multiple micro/nanocrystals and/or amorphous materials. In each SONICC measurement, approximately 2 mg of griseofulvin powder was sandwiched between a conventional microscope slide and cover slip and imaged.

Figure 2:
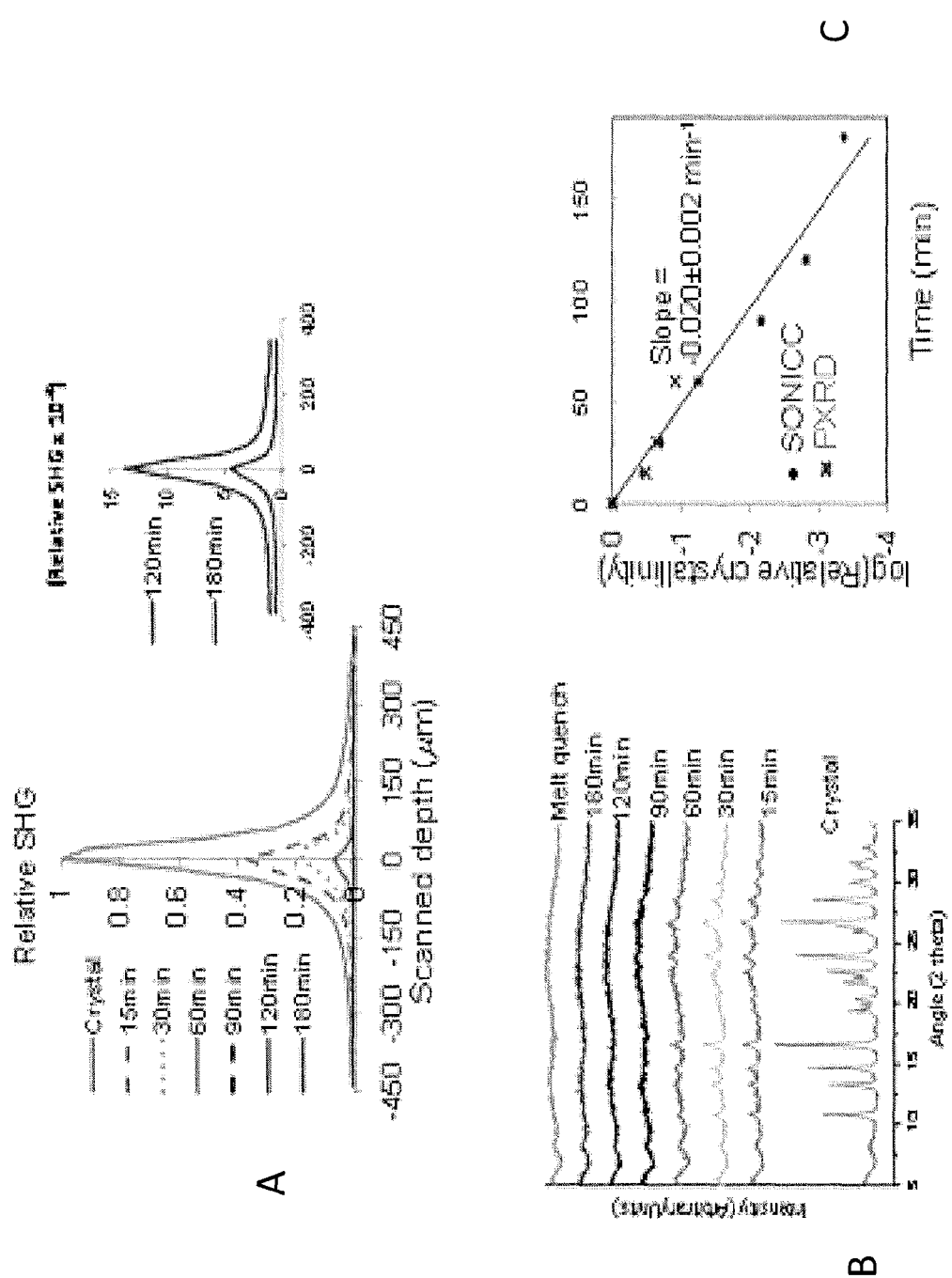
FIG. 2 shows: (A) relative SHG of pure crystalline and cryomilled griseofulvin; (B) PXRD of griseofulvin powder prepared by cryomilling at different period of time and melt quenching; and, (C) Macroscopic relative crystallinity estimated by SONICC and PXRD.

A comparison of the percentage crystallinity of cryomilled samples of griseofulvin as a function of time, determined using both SONICC and PXRD is shown in FIG. 2. The percentage crystallinity of cryomilled griseofulvin decreases as the milling time increases, consistent with previous studies for both griseofulvin and other organic compounds and demonstrating mechanically induced crystallinity loss. In addition PXRD did not show any broadening of the Bragg peaks with increases in milling time. Peak broadening may be an indication of nanostructure formation. The PXRD method allows for the detection of residual crystallinity after milling for 60 minutes, corresponding to approximately 12% crystallinity. At lower levels of crystallinity, the Bragg peaks disappear and a diffuse halo is present. The halo patterns of cryomilled griseofulvin (e.g., after 180 minutes milling) appear to be visibly indistinguishable from the pattern of melt-quenched griseofulvin as shown in FIG. 2B. At this point, the material may be termed "X-ray amorphous". As discussed previously, "X-ray amorphous" may not necessarily be indicative of complete disordering of the material. Diffuse halos may arise from, for example, 1) broadening of the PXRD peak from reduction in the average crystal size to the nanocrystalline domain, but still preserving the parent crystalline unit cell; or, 2) overall loss of crystalline order to generate an amorphous phase.

After 90, 120, and 180 minutes of cryomilling, and well after griseofulvin becomes X-ray amorphous, residual crystallinity can be detected and quantified by SONICC with the percent crystallinity estimated to be 0.7%, 0.2%, and 0.04%, respectively, measured with a high signal-to-noise ratio. After 60 minutes milling, the percent crystallinity estimated by SONICC was 6%, which was significantly different than the 12% estimated by PXRD. The discrepancy between the crystallinity estimated by these two techniques may arise from a high halos background in PXRD accompanied with smaller Bragg peaks used to estimate percent crystallinity, which can significantly affect the signal-to-noise ratio in the measurement.

The detection limit of SONICC for residual crystallinity within the powder can be estimated from the intensity in a single voxel producing a signal-to-background ratio greater than 3 within the total volume probed in the field-of-view. The SHG intensity of a single voxel (4×4×20 µm$^3$) may have a broad distribution due to variations in the size and the orientation of the crystals. For a signal-to-background ratio of 3 in a single voxel, the mean detection limits (averaged over all crystallographic orientations) for percentage crystallinity may be given by the ratio of that calculated signal to the signal generated by the 100% crystalline powder. For griseofulvin under the conditions in which these data were recorded, the mean detection limits correspond to 4×10$^{-4}$%, or 4 parts-per-million, crystallinity.

The observed detection limit in the powder is significantly higher than that reported previously in uniform amorphous thin films of griseofulvin (~10$^{-9}$%, or ~10 parts per trillion) largely because of a relatively weak but nonzero background in the powder attributed to surface second harmonic generation. Significant additional measurement improvements may be possible by increasing the laser power, given the quadratic dependence of the signal on the incident intensity (Here, the laser power was kept low in the experiments described to maintain a linear detection characteristic at high percentage crystallinity). The loss of crystallinity of griseofulvin powder upon cryomilling appears to exhibit first order kinetics with respect to the duration of cryomilling (FIG. 2C), as measured by SONICC, with a rate constant of −0.020±0.002 min$^{-1}$ (8% RSD), corresponding to a half-life of 15±1 min. The first order kinetics for the reduction of crystallinity suggests that the rate at which the powder is disordered is proportional to the amount of crystalline material present. This observation in turn suggests that each crystallite has a finite statistical chance of being rendered amorphous per unit time of cryomilling. Extrapolation beyond the experimentally demonstrated 4 decades of dynamic range suggests that milling times of 5 hours would be required to achieve a residual crystallinity of 1 part per million, which is still well above the estimated detection limit of the instrument.

Additional insights into the physical action of cryomilling, not provided by ensemble-averaged measurements such as PXRD, can be obtained by analysis of individual crystallites from the SONICC images.

Figure 3:
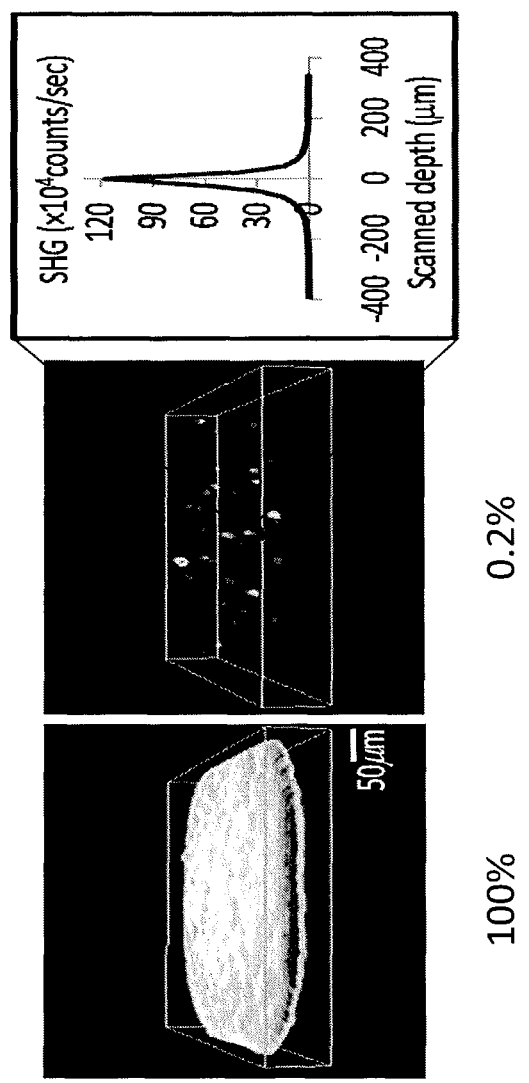
FIG. 3 shows three-dimensional SONICC images of pure (100%) crystalline and partially crystalline (0.2%) griseofulvin powders. The average SHG intensity over a particular crystallite is shown.

3-D images of pure crystalline and cryomilled (partially crystalline) griseofulvin powders were constructed from Z-plane slices of SONICC images, as shown in FIG. 3. The crystalline griseofulvin powder (FIG. 3A) exhibits SHG activity in the entire field-of-view. The cryomilled griseofulvin powder (FIG. 3B) exhibits SHG activity only at specific locations, even though the entire field-of-view was filled by highly scattering powder. These 3-D images suggest that the residual macroscopic crystallinity, after exhaustive milling, arises primarily from a small fraction of well localized crystalline domains, rather than a uniform distribution of weakly-SHG-generating centers. That is, the majority of the sample becomes SHG amorphous. This state may be characterized as the essential absence of SHG activity due to the loss of crystalline order in the solid.

Although there are several low-throughput tools, e.g. scanning electron microscopy and atomic force microscopy, facilitating high-resolution imaging of particles and providing information on solid state (amorphous, crystalline) and morphology, they are only suitable for surface, rather than bulk material characterization. The results shown in FIG. 3 thus demonstrate the use of SONICC for rapid visualization of phase heterogeneities within a bulk powder that are not easily accessible at a comparable spatial/temporal resolution using other well-established techniques.

The use of SONICC to visualize individual crystallites within the bulk material in such highly-scattering samples is useful, particularly when compared to conventional bright-field images of the identical samples. The capability of SONICC to provide image contrast interior to turbid matrices may be attributed to: 1) the high degree of selectivity of SHG response to crystalline material, 2) the use of a long wavelength (infrared) incident energy beam to minimize scattering, and 3) the general insensitivity of nonlinear optical measurements to optical scatter shared by multi-photon excited fluorescence. Since only the unscattered or unrefracted light arriving at the focal volume contributes to the generation of a SHG signal, the detected SHG light is considered to have arisen from that same focal volume element. Scattering of the incident fundamental beam may reduce the relative fraction of the light reaching the focal volume, which in turn can impact the local intensity of the generated SHG, but not the spatial resolution thereof. Furthermore, the detected SHG will have arisen from that same focal volume, irrespective of the number of scattering events experienced by the SHG light prior to detection. In practice, a single-channel photomultiplier tube detector was used and positioned to optimize detection of all SHG light collected through the objective.

Figure 4:
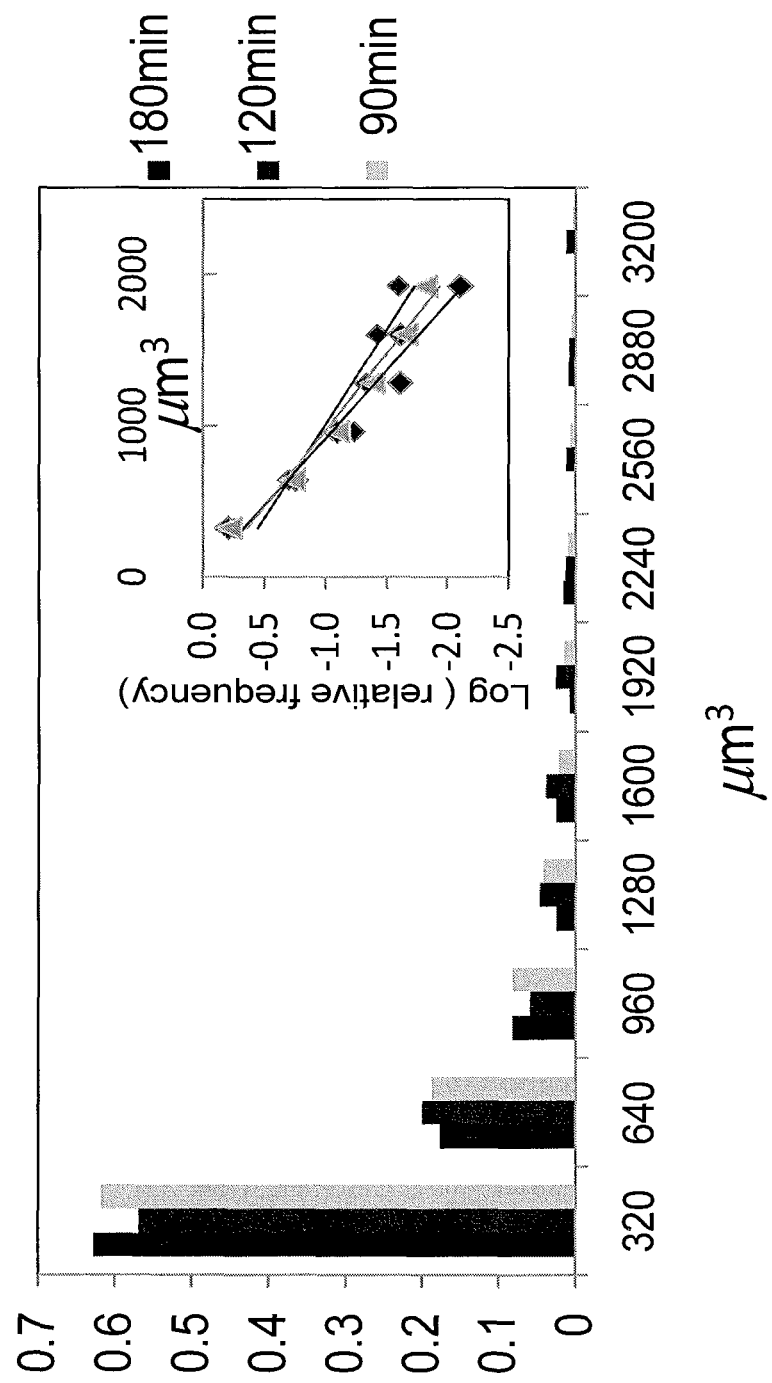
FIG. 4 shows the normalized crystal size distribution of cryomilled griseofulvin powder for different milling times.

Visualization of individual crystallites permits assessing crystal size distributions (CSD), which are routinely estimated during crystallizations from liquids and solutions by monitoring light scattering. FIG. 4 shows the crystal size distribution of cryomilled griseofulvin as a function of time (for example, 90 to 180 min milling time) analyzed by SONICC. Since the crystal counting algorithm did not distinguish two independent crystals located in adjacent voxels or in close contact, potential artifacts from crystal coalescence (e.g., spatial overlap of separate crystals within the images) may arise at high crystal density. For example, after 60 min of milling, the largest crystal size recognized by the algorithm was $2.3 \times 10^7$ $\mu m^3$ (25% of the total volume) which is larger than the initial powder crystal size indicating that the algorithm may overestimate the crystal size. Therefore, the crystal counting was only performed on griseofulvin cryomilled for 90 min and longer, in which individual crystallites could be easily isolated within the images. The inset in FIG. 4 shows that the crystal size distributions are essentially constant between 90 and 180 min milling time suggesting that the crystals have reached their fracture limit prior to 90 minutes of milling.

Combined macroscopic and microscopic measurements can, for example, be compared against the predictions of two proposed mechanisms for the observed loss in crystallinity after cryomilling: 1) one-step process in which an intact microcrystal is rendered amorphous; or 2) a multi-step process in which larger crystals are broken down to increasingly smaller crystals. The multi-step process predicts a net increase in the relative fraction of smaller crystals with increased milling times, with corresponding differences in both the CSD and the overall detected percentage crystallinity. Conversely, the one-step mechanism suggests that each residual crystal has a finite chance of being rendered amorphous with the fall of the milling impacter, with changes observed only in the percentage crystallinity, but not in the normalized CSD.

The data of FIG. 4 suggests that there was no statistically significant change in the CSD as a function of increased milling time, despite a ~16-fold reduction in the overall percentage crystallinity of the powders. This observation is consistent with the one-step process as the dominant mechanism for loss of crystallinity within griseofulvin crystals 320 to 3200 $\mu m^3$ (or 8 to 18 $\mu m$ diameters assuming spherical particles) in size. At the microscopic level, these results are consistent with a model in which microcrystals have a finite probability of being susceptible to high enough local shear forces during the milling process to undergo substantial lattice deformations and be rendered amorphous. This observation and mechanism would also result in overall first-order kinetics for the loss in crystallinity, consistent with the results shown in FIG. 2.

Further insight into the mechanism of crystallinity loss can be obtained from calorimetric measurements. Differential scanning calorimetric (DSC) measurement of cryomilled griseofulvin was performed to assess ensemble-averaged energetics. A glass transition temperature ($T_g$), characteristic of a glassy material, was not seen for cryomilled griseofulvin because of an exothermic event occurring in the same temperature range as the expected $T_g$, in agreement with previous reports. Similar to previous study, a bimodal exothermic event was observed. This bimodal exotherm may be a result of surface crystallization (lower temperature) versus bulk crystallization (higher temperature). Herein, the magnitude of this exothermic event may be used to assess the extent of recrystallization on heating of the cryomilled material and by inference, the extent of the crystal-to-glass phase transformation induced on milling.

The enthalpy associated with the recrystallization of the 3h cryomilled sample was −52.51 J/g while the theoretical enthalpy of the liquid to crystal phase transformation (estimated from the heat capacity adjusted enthalpy of fusion, and thermodynamic parameters) was estimated to be −53.76 J/g. Considering the experimental uncertainties associated with the DSC methodology, these results are not significantly different. Hence, close to 100% of the excess enthalpy imparted to the sample by mechanically induced disordering during cryomilling was recovered upon recrystallization, confirming that residual crystallinity within the sample represents a low total-mass-fraction of the material, as suggested by the SONICCS results shown in FIG. 2. The calorimetric data thus support a crystal-to-glass transformation on cryomilling rather than the formation of a nanocrystalline material where, for the latter system, the enthalpy recovered during heating would be expected to be only approximately 40% of the heat of fusion. Similar energetic properties have been observed previously for different organic compounds exposed to exhaustive milling.

Considering the apparent presence of crystalline seeds in the cryomilled sample, the sample may be expected to display different crystallization kinetics from a glass prepared by rapid quenching of a melt; the presence of residual crystallinity can potentially act as a source for secondary nucleation of the same polymorph or heterogeneous nucleation of a different polymorph.

Individual nanocrystalline domains of griseofulvin smaller than ~90 nm in diameter may be approaching the detection limits of the specific SONICC measurement apparatus used, such that SONICC would not distinguish directly between truly amorphous materials and materials containing crystalline domains much smaller than this limit. Isothermal recrystallization kinetics were monitored at 50° C. for cryomilled and melt-quenched griseofulvin using SONICC and FIG. 5A depicts time-dependent 2-D slices of 3-D SONICC images. The overall crystallization rate for cryomilled griseofulvin is significantly faster (40-fold) than the melt-quenched counterpart. Microscopically, evolution of microcrystals within cryomilled griseofulvin appears to be nearly uniform and individual nucleation sites were not observed. Recrystallization of melt-quenched griseofulvin, on the other hand, demonstrates stochastic crystal nucleation with the induction time of 20 minutes and with subsequent growth of the nucleation centers. These combined results suggest the residual presence of numerous ordered domains, over and beyond the residual crystallinity shown in FIG. 3, which may be capable of nucleating barrier-less crystal growth in the cryomilled powders that are not present in melt-quenched powders. Based on the calorimetric data, these seeds represent a low total-mass-fraction of the sample.

Figure 5:
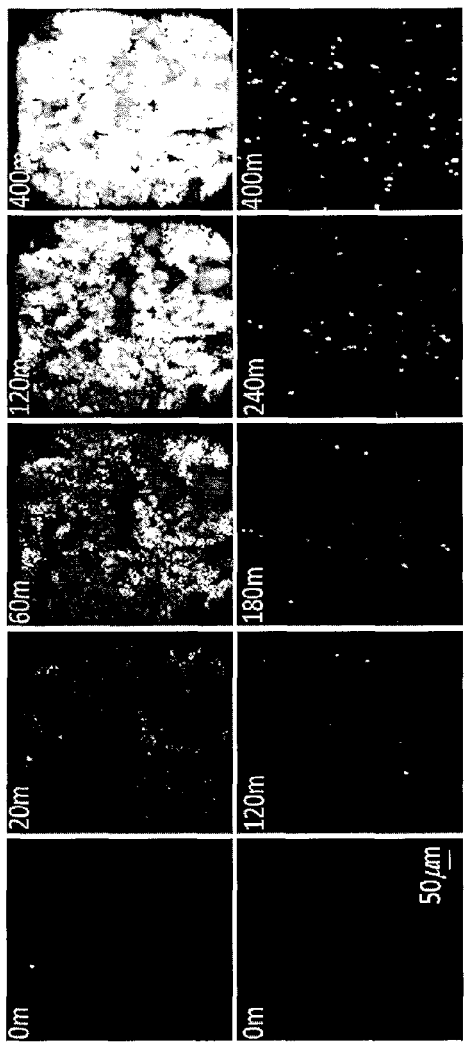
FIG. 5 shows: (A) Isothermal recrystallization at 50° C. of 3 hr-cryomilled (top) and melt-quenched griseofulvin (bottom) monitored by SONICC; (B) integrated SHG intensity as a function of time; and, (C) a DSC thermogram of cryomilled griseofulvin.
Figure 5:
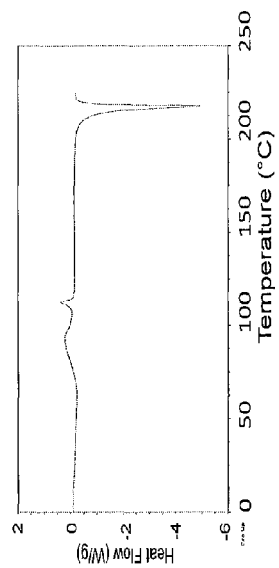
Figure 5:
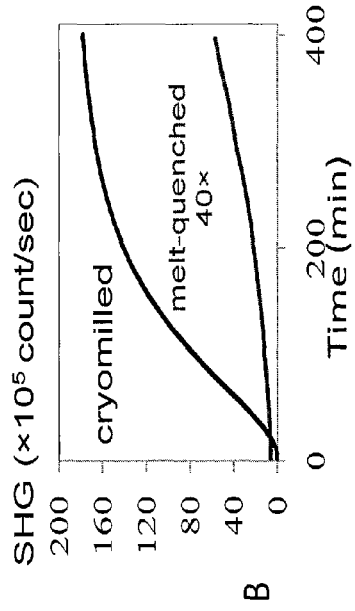

The discrepancy in recrystallization of cryomilled and melt-quenched griseofulvin shown in FIG. 5 is should be noted. A lack of crystallization induction time (on the time scale of SONICC acquisition), unobserved nucleation sites, and a rapid crystallization within cryomilled powder may suggest that residual crystalline domains remain that were larger than the critical size for nucleation, but below the single-crystal detection limits of SONICC apparatus used. By effectively eliminating the energetic barrier for nucleation, the overall crystallization rate depended only on the crystal growth kinetics.

The crystallization behavior of naproxen within an amorphous polymer matrix (methoxy-polyethylene glycol, or mPEG) was obtained as a function of temperature. Naproxen was purchased from Spectrum Chemical Supply (Gardena, Calif.), and mPEG with molecular weight (MW) of 3,350 was furnished by the Dow Chemical Company. The tablets were prepared by first physically mixing naproxen and mPEG. This mixture was placed onto a Teflon-coated metallic hot plate, and melted at 150° C. Once melted, the sample was covered with another Teflon-coated metal plate. The distance between the top and bottom Teflon-coated surfaces determined the final thickness of the tablets. The two temperature comparison points utilized were 25° C. and 40 C. Amorphous tablets of naproxen in mPEG20, pluronic 87, and PEG60 were prepared similarly.

Figure 6:
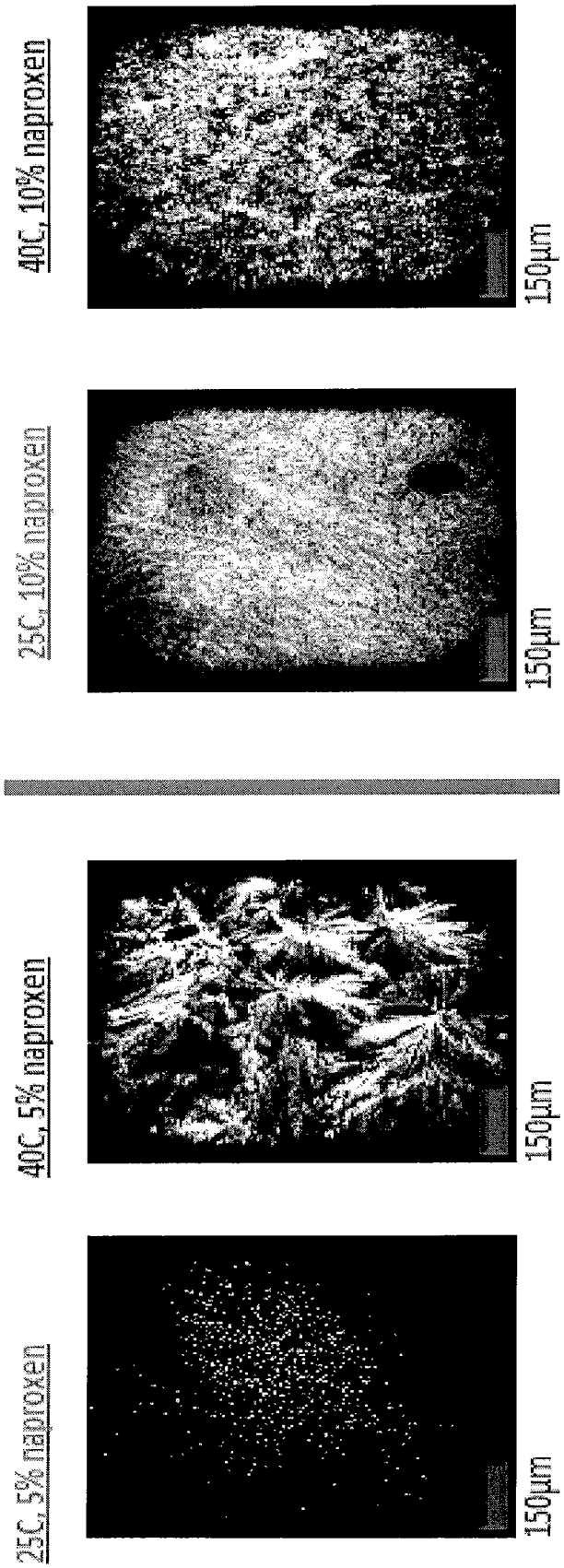
FIG. 6 shows a comparison of 4 naproxen/PEG tablets with two different loadings, solidified at two different temperatures; a 10× objective with field of view ~600×600 μm was used.
Figure 7:
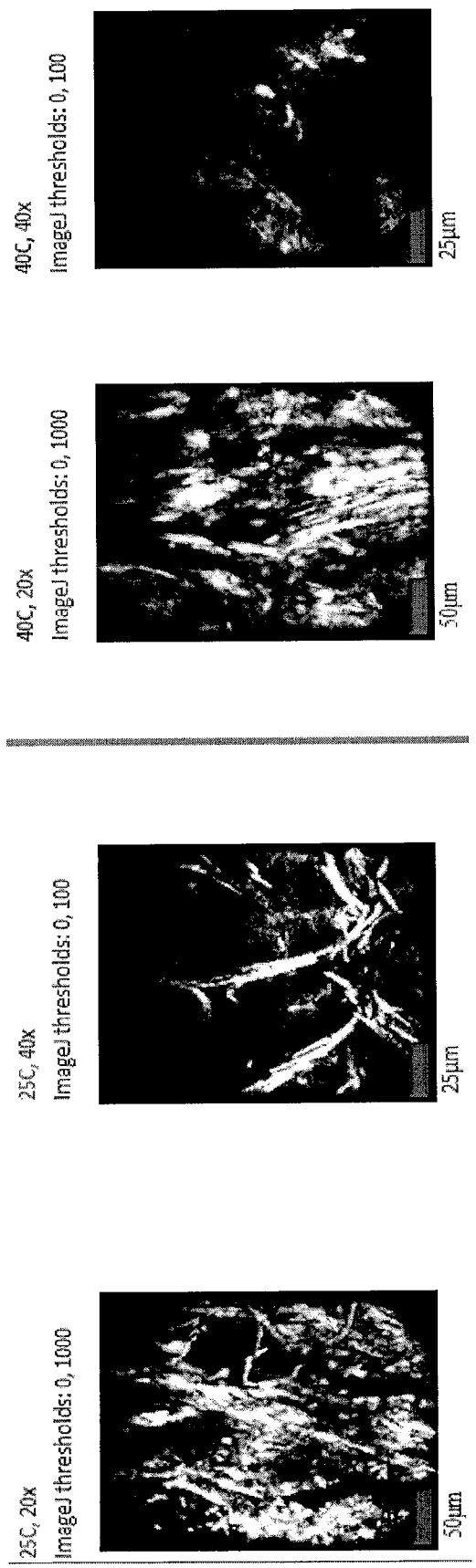
FIG. 7 shows images of 1 5% naproxen in PEG, solidified at 25° C. and 40° C., and imaged at 20× and 40×; all with unique fields of view. Thresholds shown are the minimum and maximum displayed values using ImageJ image processing.

The tablet analysis was performed initially by Z-scanning with a 10× objective, individual slices of which are shown in FIG. 6 for naproxen/mPEG blends.

The thresholds of all of the images in FIG. 5 were the same in the image analysis software, ImageJ. At 25° C., the 5% naproxen tablet was mostly amorphous. Measurements were repeated with freshly prepared tablets at greater magnifications, showing the same trend of the crystalline domains in the tablets that solidified at 40° C. being larger overall than the tablets solidifying at 25° C.

From inspection of the SONICC images, the spatial distribution of the crystalline API within the tablet and the crystal size distribution appear to be significantly affected by the thermal history of the tablets.

Sample preparation for these experiments consisted of preparing various concentrations of naproxen in HPMCAS (Hydroxypropylmethylcellulose Acetate Succinate) as an excipient. HPMCAS was acquired from Shin-Etsu Chemicals (Tokyo, Japan), and naproxen was acquired from Sigma-Aldrich (St. Louis, Mo.). The concentrations prepared include: 0, 0.1, 0.5, 1, 2, 5, 7.5, 15, 25, 35, 50, 65, 75, 90 and 100% naproxen-HPMCAS (% w/w). The samples were cryogenically milled via a 6750 series Spex Sampleprep (Metuchen, N.J.) freezer mill. The samples were equilibrated to liquid nitrogen temperatures for five minutes prior to milling. Milling consisted of two cycles of two minute milling, and a rest interval of one minute between the two cycles. Following the completion of milling, the samples were placed in to a nitrogen-filled glove box to allow the sample to return to room temperature without being influenced by moisture. Three unique sets of samples were prepared to allow for comparison.

Solid dispersion samples of naproxen and HPMCAS were prepared for comparison via a rotary evaporator. Naproxen and HPMCAS (75% w/w naproxen) were dissolved in a 1:1 w/w mixture of ethanol and dicholoromethane, were placed into a rotary evaporator, kept under vacuum for 48 hours, and then stored at 55° C. The purpose of the solid dispersion samples was to compare the time when crystals could be detected. The term "solid dispersion" refers to a group of solid products consisting of at least two different components, generally a hydrophilic matrix and a hydrophobic drug.

Figure 8:
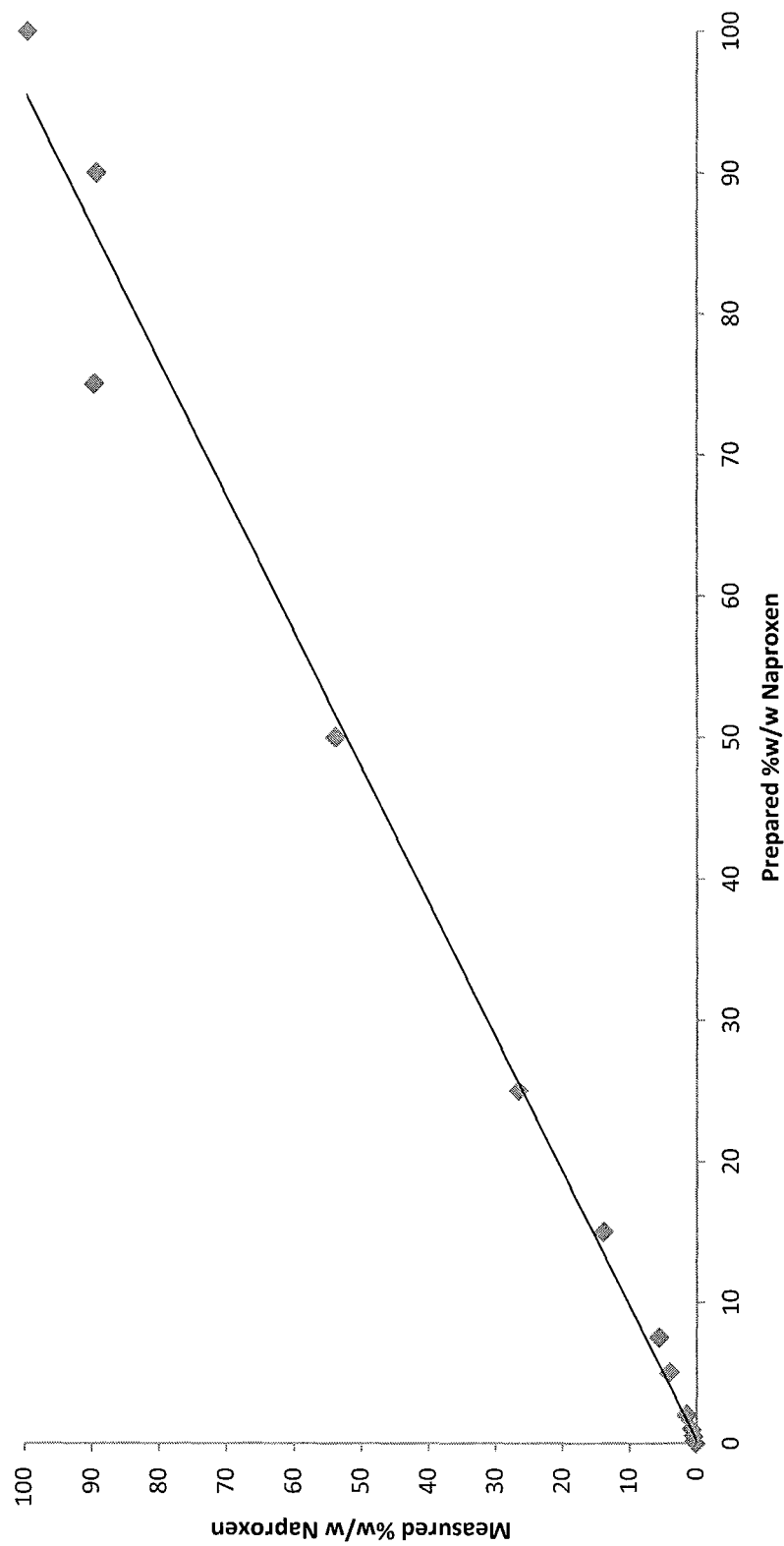
FIG. 8 shows a graph of the amount of naproxen present within an HPMCAS matrix, normalized with 100% naproxen.
Figure 9:
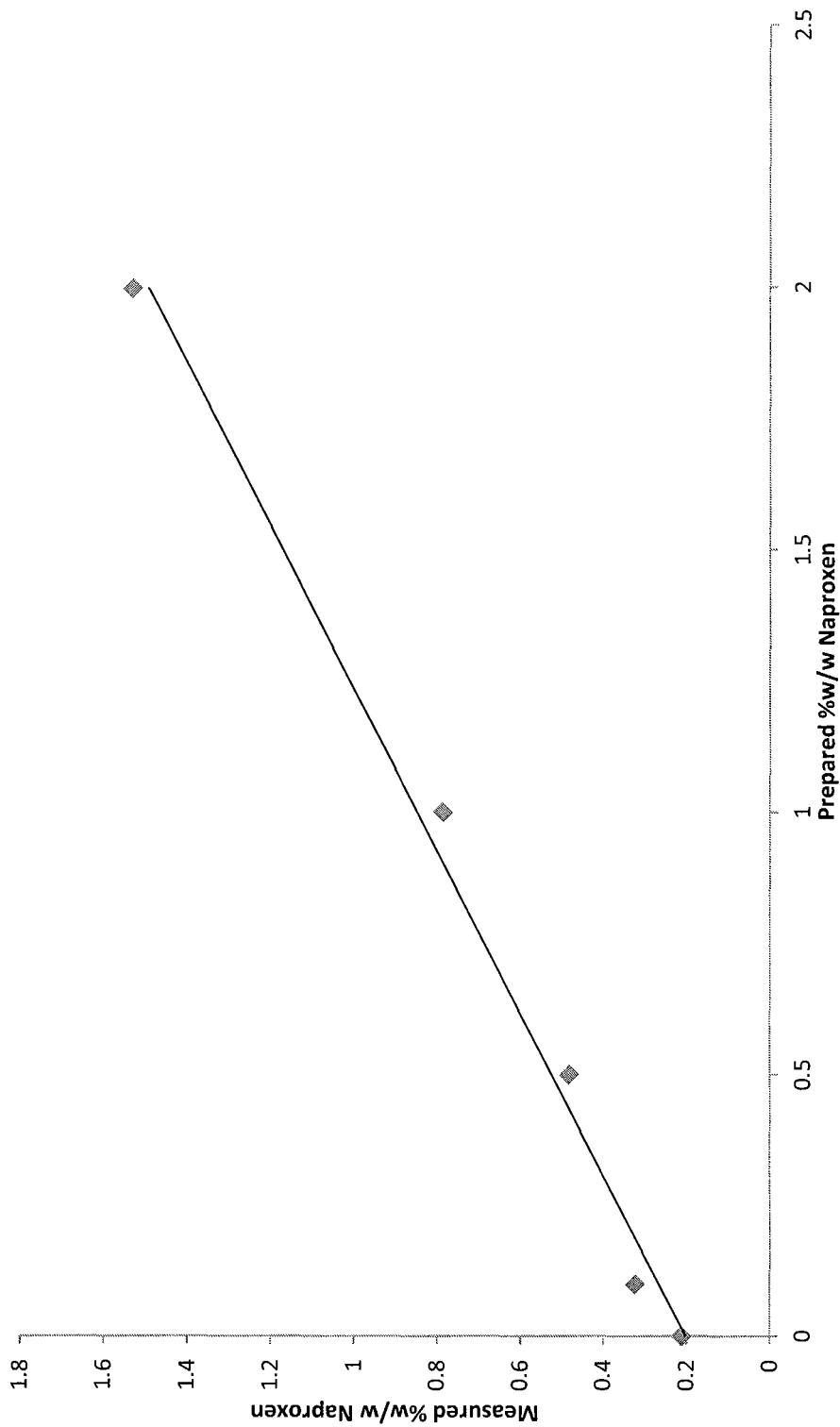
FIG. 9 shows an enlargement of FIG. 8 for lower preparation percentages.

FIGS. 8 and 9 show calibration curves for the samples that were prepared in triplicate. Samples were analyzed on the SONICC system described herein. The prepared powder sample was placed on a glass slide, bordered by two glass clover slips. The prepared powder sample was placed on a glass slide with two ~150 μm thick spacers placed at the distal ends. The sample was covered by a microscope cover glass, to create a flat-surface sample cell. This sample cell allows control of uniformity of packing of samples. The samples were all analyzed at 30 mW of laser power at the sample, with 1000 sweeps of the laser, per line, and 35 steps in the Z-direction.

Crystal nucleation of bulk API powders was monitored in real-time using SONICC. For sample preparation in the nucleation experiments, Griseofulvin ((2S,6'R)-7-chloro-2', 4,6-trimethoxy-6'-methyl-3H,4'H-spiro[1-benzofuran-2,1'-cyclohex[2]ene]-3,4'-dione), was procured from Hawkins Inc. (Minneapolis, Minn.). The samples were prepared by melting, and then rapidly quenching by liquid nitrogen. The quench-cooled samples were initially purely amorphous. The samples were then ground at the cryogenic temperature with nitrogen gas consistently purged. The ground powders were then sieved to isolate particle size in the range of 50-150 μm.

Figure 10:
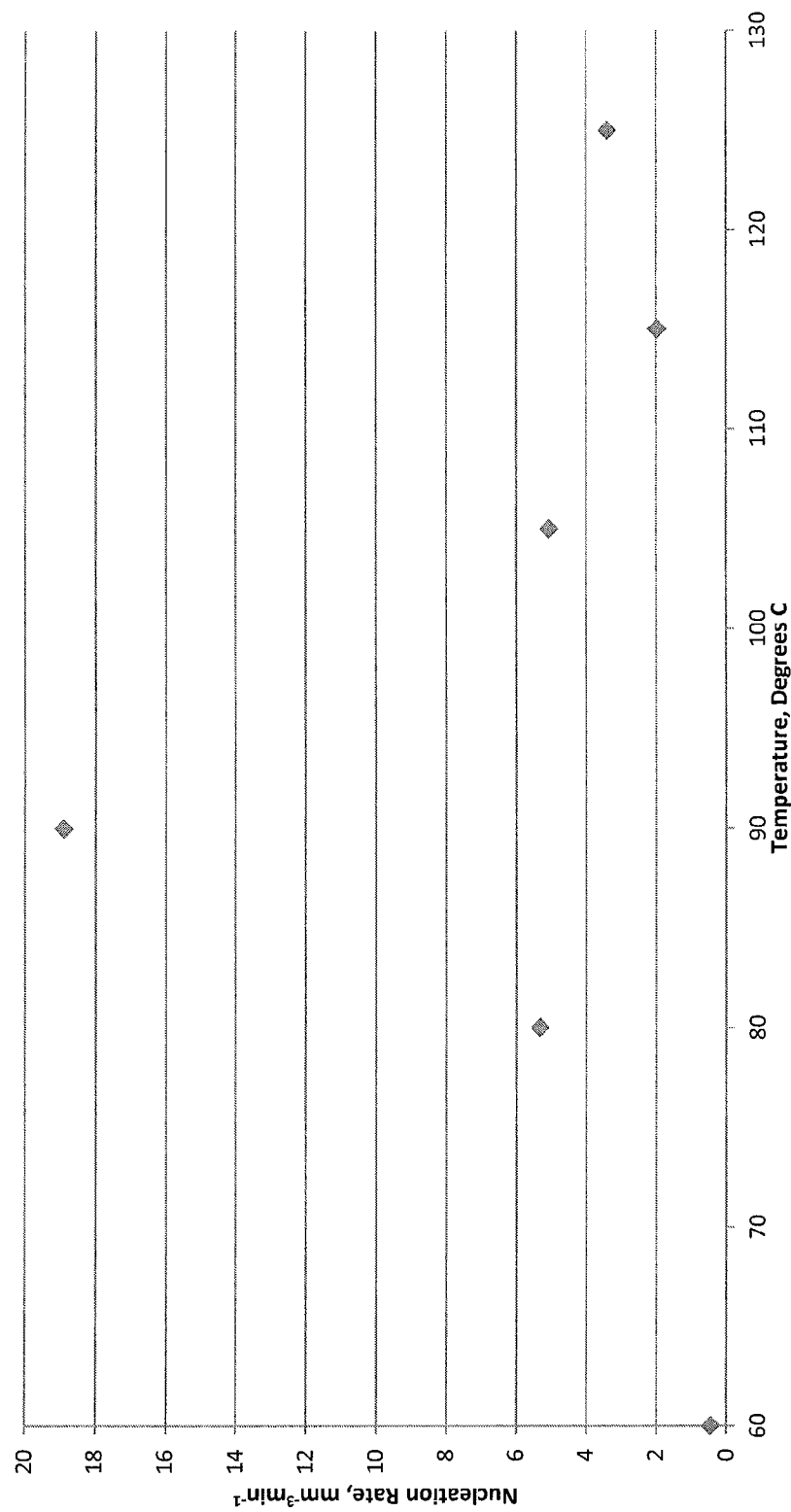
FIG. 10 shows a graph of the nucleation rate of griseofulvin.

Crystal nucleation at different temperatures was monitored. Temperature control was achieved using a temperature control stage (Linkam Scientific Instruments). Rates of nucleation were estimated from the change of crystal number density as a function of time; where the crystal number density was analyzed using a 3-D particle counting algorithm in Image J. The maximum heating rate of the stage was 100° C./min, and this was found to be relatively slow for the acquisition of the higher temperature data points. FIG. 10 shows data acquired by temperature ramping from ambient to temperatures between 60° and 125° C. The higher temperature points are potentially inaccurate, as it took approximately 1 minute to reach the correct temperature.

It will be appreciated that the methods described or the apparatus may be configured or embodied in part in machine-executable instructions, e.g. software, or in hardware, or in a combination of both. The instructions can be used to cause a general-purpose computer, a special-purpose processor, such as a DSP or array processor, or the like, that is programmed with the instructions to perform the operations described. Alternatively, the operations might be performed by specific hardware components that contain hardwired logic or firmware instructions for performing the operations described, or by any combination of programmed computer components and custom hardware components, which may include analog circuits.

The methods may be provided, at least in part, as a computer program product that may include a machine-readable medium having stored thereon instructions which may be used to program a computer (or other electronic devices) to perform the methods. For the purposes of this specification, the terms "machine-readable medium" shall be taken to include any medium that is capable of storing or encoding a sequence of instructions or data for execution by a computing machine or special-purpose hardware and that may cause the machine or special purpose hardware to perform any one of the methodologies or functions of the present invention. The description of a method as being performed by a computer should not preclude the same method being performed by a person.

For example, but not by way of limitation, a machine readable medium may include read-only memory (ROM); random access memory (RAM) of all types (e.g., S-RAM, D-RAM. P-RAM); programmable read only memory (PROM); electronically alterable read only memory (EPROM); magnetic random access memory; magnetic disk storage media; flash memory; or electrical, optical, acoustical data storage medium, or the like.

Certain aspects, advantages, and novel features of the claimed invention have been described herein. It would be understood by a person of skill in the art that not all advantages may be achieved in practicing a specific embodiment. The claimed invention may be embodied or carried out in a manner that achieves or optimizes one advantage or group of advantages as taught herein without necessarily achieving other advantages as may have been taught or suggested.

It is therefore intended that the foregoing detailed description be regarded as illustrative rather than limiting, and that it be understood that it is the following claims, including all equivalents, that are intended to define the spirit and scope of this invention.

What is claimed is:

1. An apparatus for measuring second harmonic generated (SHG) signals, the apparatus comprising:
 a coherent optical source producing a light beam having a first wavelength;
 a device configured to scan the light beam in a raster pattern having a field-of-view;
 a sample holder;
 a sample having a thickness of approximately 150 microns comprising a solid dispersion having a crystalline component dispersed therein and disposed in the sample holder;
 an objective lens disposed in an optical path such that the light beam is focused at a focal point within the sample;
 at least one optical filter disposed in the optical path to selectively transmit light having a wavelength that is one half the wavelength of the light beam of the pulsed coherent optical source; and
 at least one opto-electronic detector disposed to detect the filtered light,
 wherein the sample holder and the objective lens are configurable with respect to each other such that the field-of-view of the raster pattern is stepped to a plurality of selectable locations for repeatedly imaging the sample and the depth of focus of the light beam is less than one fifth of the thickness of the sample.

2. The apparatus of claim 1, wherein the raster pattern is focused at a selected depth in the sample positioned by the sample holder.

3. The apparatus of claim 1, further comprising a dichroic mirror disposed between the raster scan device and the sample holder.

4. The apparatus of claim 1, wherein a filter of the at least one filter is a dichroic mirror.

5. The apparatus of claim 1, wherein the crystalline component is an active pharmaceutical ingredient (API).

6. The apparatus of claim 5, wherein the solid dispersion further comprises at least one of methoxy-polyethylene glycol (mPEG) or polyethylene glycol (PEG).

7. The apparatus of claim 1, wherein the sample holder further comprises a temperature-controlled heating element.

8. The apparatus of claim 1, wherein the sample is a powder.

9. The apparatus of claim 1, wherein the at least one optical filter comprises a first filter and a second filter, each filter disposed in the optical path so forward-propagated SHG energy and backward-propagated SHG energy from the sample are detected by a first opto-electronic detector and a second opto-electronic detector of the at least one opto-electronic detector.

10. A method of measuring crystalline structures disposed in an amorphous matrix, the method comprising:
 providing a second harmonic generation (SHG) apparatus, the apparatus comprising:
 a coherent light source;
 a sample holder;
 a raster scan device to direct light of the coherent light source onto the sample holder through an objective lens;
 an optical detector, configured to detect energy at half of the wavelength of the coherent light source;
 providing a sample having a thickness of approximately 150 microns, comprising a solid dispersion having a material with a crystalline component dispersed therein, wherein a value by weight of the crystalline sample is less than about 2 percent of the sample weight;
 disposing the sample in the sample holder; and
 repeatedly indexing a field-of-view of the raster scan device over an area greater than that of the field-of-view;
 focusing light from the coherent light source at a plurality of selectable depths within the sample; and
 collecting raster-scan SHG intensity data at depths of the selectable depths,
 wherein a depth of focus is less than one-fifth of the thickness of the sample.

11. The method of claim 10, wherein forward scattered and backscattered SHG intensity is measured simultaneously.

12. The method of claim 10, further comprising:
 processing the raster-scan SHG intensity data to form a three dimensional image of a portion of the sample.

13. The method of claim 10, wherein the optical detector is positioned to detect at least one of forward-scattered SHG intensity or backscattered SHG intensity.

14. The method of claim 10, wherein the sample is solid dispersion further comprising at least one of methoxy-polyethylene glycol (mPEG) or polyethylene glycol (PEG).

15. The method of claim 14, wherein the sample further comprises an active pharmaceutical ingredient (API).

16. The method of claim 10, wherein a temperature of the sample in the sample holder is controlled.

17. The method of claim 10, wherein the amorphous matrix consists of a same powdered active pharmaceutical ingredient rendered amorphous by extensive milling.

18. The method of claim 1, wherein the amorphous matrix consists of a powdered blend comprising the crystalline active pharmaceutical ingredient and an excipient.

19. The method of claim 10, wherein the weight component of the crystalline component is less than 1 percent of the sample weight.

20. The method of claim 10, wherein the SHG intensity data is normalized with respect to a SHG intensity value of a pure sample of the material with the crystalline component to determine the volumetric percentage of the crystalline component.

21. The apparatus of claim 1, wherein the sample has a crystalline component having a value by weight of less than about two percent of an overall sample weight.

22. The method of claim 10, wherein the raster scan SHG data obtained by repeatedly indexing the field of view and focusing the light at a plurality of depths is used for:
    forming a time history of the rate of change of the crystalline component.

* * * * *